United States Patent [19]

Umemura et al.

[11] 4,078,006

[45] Mar. 7, 1978

[54] PROCESS FOR PREPARING DIHYDRIC PHENOL DERIVATIVES

[75] Inventors: Sumio Umemura; Nagaaki Takamitsu; Toshikazu Hamamoto; Nobuyuki Kuroda, all of Ube, Japan

[73] Assignee: UBE Industries, Ltd., Ube, Japan

[21] Appl. No.: 682,064

[22] Filed: Apr. 30, 1976

Related U.S. Application Data

[63] Continuation-in-part of Ser. No. 558,700, Mar. 17, 1975, abandoned.

[30] Foreign Application Priority Data

Apr. 4, 1974 Japan .................................. 49-37318
May 7, 1974 Japan .................................. 49-49811

[51] Int. Cl.$^2$ ........................................... C07C 39/08

[52] U.S. Cl. ................................. 260/621 G; 260/625
[58] Field of Search ................ 260/621 R, 625, 621 G

[56] References Cited

U.S. PATENT DOCUMENTS 3,481,989 12/1969 Vesely .................................. 260/613
3,849,502 11/1974 Bourdin et al. ................. 260/613 D

*Primary Examiner*—James O. Thomas, Jr.
*Assistant Examiner*—Werren B. Lone
*Attorney, Agent, or Firm*—Flynn & Frishauf

[57] ABSTRACT

A process for preparing dihydric phenol derivatives by oxidizing monohydric phenol derivatives with hydrogen peroxide in the presence of a ketone. This reaction can be promoted in the presence of sulfuric acid or a salt thereof or a sulfonic acid or a salt thereof.

17 Claims, No Drawings

PROCESS FOR PREPARING DIHYDRIC PHENOL DERIVATIVES

RELATED APPLICATION

This application is a continuation-in-part of application Ser. No. 558,700, filed Mar. 17, 1975, now abandoned.

This invention relates to a process for preparing dihydric phenol derivatives. More particularly, it is concerned with a process for preparing dihydric phenol derivatives having the formula (I):

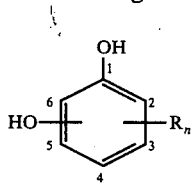

wherein each R represents a lower alkyl radical having 1-6 carbon atoms and each R may be the same or different, and $n$ represents zero or an integer from 1 to 4 and when $n$ is 3 or 4, there is no case where all of the 2-, 4-, and 6-positions are occupied with alkyl radicals, which comprises oxidizing a monohydric phenol derivative having the formula (II):

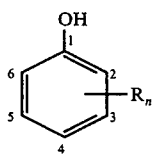

wherein R and $n$ have the same meanings as above with hydrogen peroxide in the presence of a ketone.

In regard to the preparation of catechol and hydroquinone through oxidation of phenol, many processes have been proposed. For instance, oxidation of phenol with hydrogen peroxide in the presence of ferrous sulfate, copper sulfate, etc., has been known (Journal fur Praktische Chemie N.F., Vol. 159, p. 45 (1939), Von A. Chwala and M. Pailer). And, there has recently been reported a process wherein phenol is oxidized in the presence of a metal ion such as bismuth, molybdenum, vanadium, titanium, etc. (British Pat. No. 1,332,420), a process wherein phenol is oxidized with hydrogen peroxide and an organic peracid in the presence of a strongly acidic sulfonic acid type ion exchange resin (Japanese patent provisional publication No. 36130/1973), a process wherein phenol is oxidized with hydrogen peroxide in the presence of trifluoroacetic acid, and acid of pH 0.7-3 and an organic carboxylic acid (Belgian Pat. No. 786,368), and so forth. These processes, however, give poor yields of dihydric phenols upon the hydrogen peroxide or organic peracid employed.

As to the previously known principal process for preparing dihydric alkylphenols through oxidation of a monohydric alkylphenol, there may be mentioned such a process as disclosed in West German patent application provisionally published specification (Offenlegungsschrift) No. 2,064,497. In this specification is disclosed a process wherein various phenols or derivatives thereof are reacted with hydrogen peroxide in the presence of a strong acid and, in some cases, in an inert organic solvent such as 1,2-dimethoxyethane, chloroform or ethylene dichloride. Also, in respect to the reaction of a monohydric alkylphenol, an illustrative example is given therein wherein p-cresol is oxidized with perchloric acid, phosphoric acid and hydrogen peroxide without the particular presence of an organic solvent to form 1,2-dihydroxy-4-methylbenzene. However, it is noted that the yield in the example seems to be unsatisfactory.

We have conducted research into a process for preparing the desired compounds having the formula (I), which is a technically simple procedure, in a remarkably high yield of dihydric phenol derivatives upon the hydrogen peroxide employed and commercially inexpensive, and thus we have completed the present invention.

It is, accordingly, an object of this invention to provide a process for preparing dihydric phenol derivatives in a high yield upon the hydrogen peroxide employed.

Another object of this invention is to provide a commercially advantageous process for preparing the desired compounds at a low cost.

Still another object of this invention is to provide a reaction process wherein the desired compounds can be readily separated from the reaction mixture.

Other objects and advantages of this invention are apparent from the following explanation and examples.

This invention is concerned with a process for preparing dihydric phenol derivatives (I) which comprises oxidizing monohydric phenol derivatives (II) with hydrogen peroxide in the presence of a ketone. According to the process of the present invention, the dihydric phenol derivatives (I) can be prepared in a higher yield as compared with the prior process and a step for the separation of the produced dihydric phenol derivatives from the reaction mixture can be readily accomplished, since an oxidizing agent, hydrogen peroxide, is converted to water after completion of the reaction. Moreover, this process can be considered as commercially advantageous, since the desired dihydric phenol derivatives (I) are obtainable in a high yield in terms of a ratio to the hydrogen peroxide employed.

When $n$ represents zero, it is clear that the formula (II) contains phenol.

R, which is used in formulas (I) and (II), represents a straight or branched alkyl radical having 1–6 carbon atoms. As said alkyl group may be mentioned, for example, methyl, ethyl, propyl, isopropyl, butyl, sec-butyl, tert-butyl, isobutyl, pentyl, hexyl, etc. As the monohydric alkylphenols having such alkyl groups may be mentioned, for example, o-, m- or p-cresol, o-, m- or p-ethylphenol, o-propylphenol, p-isopropylphenol, m-butylphenol, p-sec-butylphenol, p-tert-butylphenol, m-isobutylphenol, p-pentylphenol, p-hexylphenol, 2,3-dimethylphenol, 2,5-dimethylphenol, 3,4-dimethylphenol, 2,4-dimethylphenol, 2,6-dimethylphenol, 3,5-dimethylphenol, 2,3,4-trimethylphenol, 2,3,6-trimethylphenol, 2,4,5-trimethylphenol, 2,3,5-trimethylphenol, 3,4,5-trimethylphenol, 2,3,4,5-tetramethylphenol, 2,3,5,6-tetramethylphenol, 2-ethyl-3-methylphenol, 3-tert-butyl-4-methylphenol, 2-isopropyl-5-methylphenol, 2-pentyl-6-methylphenol, 3-hexyl-5-methylphenol, and the like.

This invention will be explained in detail hereinbelow.

The ketones which may be employed in the present invention may be any ketones and, for instance, may be mentioned as follows:

(1) a ketone having 3–20 carbon atoms and represented by the following general formula (III):

$$R_1-CO-R_2 \tag{III}$$

wherein $R_1$ and $R_2$ may be the same or different and each represents a straight or branched alkyl group of 1-18 carbon atoms or phenyl group, the hydrogen of said alkyl groups being optionally substituted with a halogen atom, hydroxy group, amino group or phenyl group, and $R_1$ and/or $R_2$ may be an aliphatic group having an unsaturation bond;

(2) a diketone having 3-20 carbon atoms and represented by the following general formula (IV):

$$\underset{R_1-C-(CH_2)_n-C-R_2}{\overset{O\quad\quad O}{\|\quad\quad\|}} \tag{IV}$$

wherein $n$ is zero or an integer from 1 to 16, inclusive, and $R_1$ and $R_2$ have the same meanings as above;

(3) a cycloketone having the following general formula (V):

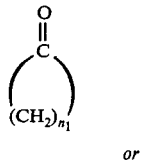 or 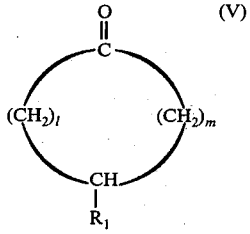

wherein $n_1$ represents an integer of 4-11, inclusive, $l + m$ represents an integer of 3-10, inclusive, and $R_1$ has the same meaning as above.

In an aliphatic ketone having the above-mentioned general formula (III), examples of the straight or branched alkyl groups of 1-18 carbon atoms in $R_1$ and $R_2$ are as follows: methyl, ethyl, propyl, 1-methylethyl, butyl, 1-methylpropyl, 1,1'-dimethylethyl, 2-methylpropyl, pentyl, 1-methylbutyl, 2-methylbutyl, 3-methylbutyl, 1,2-dimethylpropyl, hexyl, 1-methylpentyl, octyl, decyl, undecyl, 2-dodecyl, tridecyl, tetradecyl, pentadecyl, octadecyl, etc.

Representative examples of the aliphatic ketones having the above-mentioned alkyl groups are as follows:

Acetone, methylethylketone, 2-pentanone, 3-pentanone, 3-methyl-2-butanone, 2-hexanone, 3-hexanone, 3-methyl-2-pentanone, 4-methyl-2-pentanone, 3,3-dimethyl-2-butanone, 2-heptanone, 3-heptanone, 4-heptanone, 2,4-dimethyl-3-pentanone, 2-octanone, 6-methyl-2-heptanone, 2-nonanone, 2,6-dimethyl-4-heptanone, 2,2,4,4-tetramethyl-3-heptanone, 3-decanone, 6-undecanone, 2-tridecanone, 7-tridecanone, 2-tetradecanone, 2-pentadecanone, 2-hexadecanone, 2-heptadecanone, 3-octadecanone, 4-nonadecanone, 5-eicosanone, etc.

Unsaturated aliphatic ketones having the above-mentioned general formula (III) may have a double or a triple bond, but a double bond is preferable. As ketones having an unsaturation bond may be mentioned the following:

3-Buten-2-one, 3-penten-2-one, 5-hexen-2-one, 4-methyl-3-penten-2-one, 6-methyl-5-hepten-2-one, 5-octen-2-one, 7-nonadecen-2-one, etc.

Examples of ketones having the above-mentioned general formula (III) which have a phenyl group or an alkyl group substituted with a halogen atom particularly chlorine atom, bromine atom, fluorine atom and hydroxy group, amino group and phenyl group, are as follows:

1-Chloro-2-propanone, 1,1,1,3,3,3-hexachloro-2-propanone, 1,1,1,3,3-pentachloro-3-fluoro-2-propanone, 1,1,1-trichloro-3,3,3-trifluoro-2-propanone, 1-chloro-3-heptanone, 3-hydroxy-2-butanone, 1-bromo-3-heptanone, 1-hydroxy-2-propanone, 4-amino-4-methyl-2-pentanone, methylphenylketone, benzophenone, 1-phenyl-2-propanone, 1-phenyl-1-butanone, 1-phenyl-3-butanone, 1-phenyl-3-pentanone, 1,3-diphenyl-2-propanone, etc.

Examples of diketones having the general formula (IV) are as follows:

2,3-Butanedione, 2,4-pentanedione, 2,5-hexanedione, etc.

Examples of cycloketones having the general formula (V) are as follows:

Cyclopentanone, cyclohexanone, 2-ethyl-1-cyclopentanone, 2-methyl-1-cyclohexanone, cyclododecanone, etc.

The reaction conditions under which monohydric phenol derivatives are oxidized with hydrogen peroxide in the presence of the above-mentioned ketones are illustrated below.

The concentration of hydrogen peroxide employed is not particularly critical, but it is preferably to conduct the present reaction under such conditions that water is present in an amount as small as possible. However, a 30-60 percent hydrogen peroxide commercially available may also be utilized. It is to be understood that a hydrogen peroxide having a concentration of not less than 60 percent may also be utilized. The molar ratio of the ketone utilized to hydrogen peroxide is not limited. The amount of ketone used may be small, but there is no critical upper limit of the amount used since excess ketone may also act as a reaction solvent. The particularly preferred amount of ketone to hydrogen peroxide is a molar ratio of 0.005-20. The molar ratio of the hydrogen peroxide used to a monohydric phenol is not particularly critical, but the molar ratio can be 0.005-1.0, preferably 0.01-0.50. The solvent, if employed or not, does not particularly affect the reaction proceedings. Where a solvent is employed, there is no particular limitation thereupon if such solvents as methylacetate, ethylacetate, ethylene diacetate, methyl benzoate, dimethyl phthalate, diethyl phthalate, etc., do not prevent oxidation reaction. When a large amount of the ketone is employed, the ketone may act as a solvent as previously explained. The reaction may be conducted at a temperature of 0°-250° C., preferably 45°-200° C. Where the reaction is to be effected at a temperature below the melting point of a phenol derivative used as starting material, the use of a solvent is essential. The reaction period may vary upon the reaction temperature, the amount of ketone and the presence and amount of a catalyst. The reaction period is not particularly critical. The reaction may be effected at atmospheric pressure, but it may be effected at a reduced pressure or under pressure. For improved yield of dihydric phenols, it is desirable in the present reaction that water be present in situ in an amount as small as possible.

The present reaction may be effected without any use of a catalyst, but the reaction is preferably conducted in the presence of the catalyst as stated below. The catalyst which may be employed in the present reaction is sulfuric acid or its salts or a sulfonic acid or its salts. As the salts of sulfuric acid may be employed various metal salts and organic base salts and there is no limitation upon the sorts of metals and organic bases. As the type of salt may be any type of a normal salt, an acidic salt, a double salt and a complex salt. Namely, there may be used any salts if they contain sulfate ion. The sulfate, if having water of crystallization, may be utilized as such. Examples of the sulfates are as follows:

Ammonium sulfate, lithium bisulfate, sodium sulfate, sodium bisulfate, magnesium sulfate, aluminum sulfate, potassium bisulfate, copper sulfate, zinc sulfate, titanium sulfate, chromium sulfate, manganese sulfate, iron sulfate, ammonium ferrous sulfate, cobalt sulfate, nickel sulfate, potassium aluminum sulfate, silver sulfate, cadmium sulfate, indium sulfate, zirconium sulfate, tin sulfate, antimony sulfate, molybdenum sulfate, ruthenium sulfate, barium sulfate, mercury sulfate, thallium sulfate, lead sulfate, cerium sulfate, hydroxylamine sulfate, dibutylamine sulfate, aniline sulfate, pyridine sulfate, piperidine sulfate, etc.

As sulfonic acids may be employed aliphatic sulfonic acids such as methanesulfonic acid, ethanesulfonic acid and the like, aromatic sulfonic acids such as benzenesulfonic acid, p-toluene-sulfonic acid, p-phenolsulfonic acid, p-aminosulfonic acid, naphthalene-α-sulfonic acid and the like, as well as sulfonic acid type resins such as strongly acidic ion exchange resins. As the salts of sulfonic acids may be employed various salts such as metal salts, organic base salts, etc., similar to the above sulfates. A catalyst may be used in a homogeneous or heterogeneous system.

In the case of the heterogeneous system, the catalyst may be applied in various forms such as a suspended state or tablet form. The amount of catalyst may vary in a wide range, but it is desirable for a statisfactory reaction rate to employ the catalyst in an amount of not less than 0.0001 percent by weight with respect to monohydric phenols.

In the foregoing, a batchwise practice of the present reaction was illustrated, but it is to be noted that a continuous reaction of the present invention may also be practiced. More specifically, there may be mentioned a process wherein a stock flow is continuously supplied to a catalyst layer for reaction, a process wherein a catalyst is suspended or dissolved in a stock flow and the resultant is passed through a reaction zone and so forth. In the latter case, the required amount of a catalyst may be determined according to the batchwise system.

For separation of the desired product after completion of the reaction, well-known procedures may be applied, as the present reaction does not involve any matters to prevent the desired product from separation and, for example, the desired product may be easily separated subjecting it to distillation, in many cases after removal of the catalyst. Namely, water, the monohydric phenols and the dihydric phenols so produced may be optionally subjected to fractional distillation. The so separated ketone and monohydric phenols may be circulated for reuse in the next reaction.

The dihydric phenol derivative (I) so produced may be obtained either of substantially one type or in a mixture of several types, depending upon the structure of the starting monohydric phenol derivatives (II).

For instance, where phenol is employed as a starting material, a mixture of catechol and hydroquinone is formed. Where an o-alkylphenol is employed as a starting material, a mixture of a 3-alkylcatechol with a 2-alkylhydroquinone is formed. Where a m-alkylphenol is employed as a starting material, a mixture of a 3-alkylcatechol, a 4-alkylcatechol and a 2-alkylhydroquinone is formed. Where a p-alkylphenol is employed as a starting material, a 4-alkylcatechol mainly is formed. where a mixture of two or more monohydric alkylphenols is employed as a starting material, dihydric alkylphenols are formed in the form of a mixture according to the above-depicted principle.

When polyalkylphenols are employed as starting material, the products are tabulated in Table 1 as follows.

Table 1

| Polyalkylphenols as starting material | Products |
| --- | --- |
| 2,3-dimethylphenol | 3,4-dimethylcatechol, 2,3-dimethylhydroquinone |
| 2,4-dimethylphenol | 3,5-dimethylcatechol |
| 2,5-dimethylphenol | 3,6-dimethylcatechol, 2,5-dimethylhydroquinone |
| 2,6-dimethylphenol | 2,6-dimethylhydroquinone |
| 3,4-dimethylphenol | 3,4-dimethylcatechol, 4,5-dimethylcatechol |
| 3,5-dimethylphenol | 3,5-dimethylcatechol, 2,6-dimethylhydroquinone |
| 2-isopropyl-5-methyl-phenol | 3-isopropyl-6-methylcatechol, 2-isopropyl-5-methyl-hydroquinone |
| 2,3,4-trimethylphenol | 3,4,5-trimethylcatechol |
| 2,3,5-trimethylphenol | 3,4,6-trimethylcatechol, 2,3,5-trimethylhydroquinone |
| 2,3,6-trimethylphenol | 2,3,6-trimethylhydroquinone |
| 3,4,5-trimethylphenol | 3,4,5-trimethylcatechol |
| 2,4,5-trimethylphenol | 3,4,6-trimethylcatechol |
| 2,3,5,6-tetramethyl-phenol | 2,3,5,6-tetramethylhydroquinone |
| 2,3,4,5-tetramethyl-phenol | 3,4,5,6-tetramethylcatechol |

The so-obtained dihydric phenol derivatives may be utilized, for example, as an intermediate for the production of a dyestuff, an antioxidant, a drug, etc., as a single product or, if obtained in the form of a mixture, as the mixture as such or after separation as required.

The process of this invention is more concretely illustrated by way of the following examples, but these examples are not limiting the process of this invention.

EXAMPLES 1–5

Examples 1–5 were effected as stated below. Into a 50 ml.-volume flask with a flat bottom, which was equipped with a reflux condenser, a thermometer, a stirrer and an outlet for liquid, were charged 10 g. (106 m. moles) of phenol, 8.20 m. moles of the ketone indicated in Table 2 and 0.300 g. (5.29 m. moles) of a 60 percent hydrogen peroxide solution and the flask was dipped in an oil bath at 170° C. The reaction mixture was stirred to conduct the reaction for 120 minutes. The reaction mixture was analyzed by gas chromatography and yields of catechol and hydroquinone are shown in Table 2 on hydrogen peroxide basis as defined hereinbelow.

$$\text{Yield of catechol (\%)} = \frac{\text{m. mole number of the catechol produced}}{\text{m. mole number of the hydrogen peroxide charged}} \times 100$$

$$\text{Yield of hydroquinone (\%)} = \frac{\text{m. mole number of the hydroquinone produced}}{\text{m. mole number of the hydrogen peroxide charged}} \times 100.$$

COMPARATIVE EXAMPLE 1

The reactions were effected in the same manner as in Example 1 except that the ketone was not added. The results are shown in Table 2.

Table 2

| Example | Ketone Sort | Amount to be added (g) | CT yield (%) | HQ yield (%) | (CT+HQ) yield (%) | CT/HQ (molar ratio) |
|---|---|---|---|---|---|---|
| 1 | 4-methyl-2-pentanone | 0.820 | 28.3 | 19.9 | 48.2 | 1.42 |
| 2 | 2-tridecanone | 1.624 | 31.7 | 20.0 | 51.7 | 1.59 |
| 3 | 2,6-dimethyl-4-heptanone | 1.164 | 35.3 | 20.4 | 55.7 | 1.73 |
| 4 | methyl phenyl ketone | 0.984 | 33.1 | 20.7 | 53.8 | 1.60 |
| 5 | 2,5-hexanedione | 0.935 | 27.2 | 19.7 | 46.9 | 1.38 |
| Comparative 1 | None | 0 | 26.6 | 13.2 | 39.8 | 2.02 |

In the table CT represents catechol and HQ represents hydroquinone. The same representations as above will be referred to hereinbelow.

EXAMPLE 6

10 g. of phenol (106 m. moles), 0.476 g. of acetone (8.20 m. moles), 0.601 g. (5.29 m. moles) of 30 percent hydrogen peroxide and 0.070 g. of sodium bisulfate ($NaHSO_4 \cdot H_2O$) were mixed together and the resulting mixture was reacted at 50° C. for 30 minutes in the same manner as in Example 1 to give 0.292 g. of catechol and 0.216 g. of hydroquinone. The total yield of catechol and hydroquinone was 87.4 percent.

EXAMPLE 7

10 g. (106 m. moles) of phenol, 0.5904 g. (8.20 m. moles) of methyl ethyl ketone, 0.601 g. (5.29 m. moles) of 30 percent hydrogen peroxide and 0.375 g. of indium sulfate ($In_2(SO_4)_3 \cdot 9H_2O$) were mixed together and the resulting mixture was reacted at 70° C. for 30 minutes in the same manner as in Example 1 to give 0.298 g. of catechol and 0.207 g. of hydroquinone. The total yield of catechol and hydroquinone was 86.8 percent.

EXAMPLES 8-11

10 g. (106 m. moles) of phenol, 8.20 m. moles of the ketone indicated in Table 3, 0.300 g. (5.29 m. moles) of 60 percent hydrogen peroxide, 0.070 g. of aluminum sulfate ($Al_2(SO_4)_3 \cdot 18H_2O$) (miligramion 0.315 of $SO_4^{--}$) were mixed together and the resulting mixture was reacted at 100° C. for 30 minutes in the same manner as in Example 1. Yields of catechol and hydroquinone are shown in Table 3.

Table 3

| Ex. | Ketone Sort | Amount to be added (g) | CT yield (%) | HQ yield (%) | (CT+HQ) yield (%) | CT/HQ (molar ratio) |
|---|---|---|---|---|---|---|
| 8 | 4-methyl-2-pentanone | 0.820 | 50.2 | 39.9 | 90.1 | 1.26 |
| 9 | 2-tridecanone | 1.624 | 45.0 | 31.3 | 76.3 | 1.44 |
| 10 | methyl phenyl ketone | 0.984 | 49.5 | 35.5 | 85.0 | 1.39 |
| 11 | cyclopentanone | 0.689 | 47.2 | 30.2 | 77.4 | 1.56 |

EXAMPLES 12-27

To a mixture of 10 g. (106 m. moles) of phenol, 0.820 g. (8.20 m. moles) of 4-methyl-2-pentanone and 0.300 g. (5.29 m. moles) of 60 percent hydrogen peroxide was added the catalyst indicated in Table 4, and the reaction was effected at 100° C. for 30 minutes in the same manner as in Example 1. The reaction in Example 26 was effected at 160° C. for 1 hour. Yields of catechol and hydroquinone are shown in Table 4.

Table 4

| Ex. | Catalyst Sort | Amount to be added (g) | CT yield (%) | HQ yield (%) | (CT+HG) yield (%) | CT/HQ (molar ratio) |
|---|---|---|---|---|---|---|
| 12 | $H_2SO_4$ | 0.036 | 50.6 | 31.5 | 82.1 | 1.61 |
| 13 | $NaHSO_4 \cdot H_2O$ | 0.101 | 54.4 | 41.7 | 96.1 | 1.30 |
| 14 | $NaHSO_4 \cdot H_2O$ | 0.010 | 50.3 | 39.8 | 90.1 | 1.26 |
| 15 | $KHSO_4$ | 0.101 | 57.7 | 39.4 | 97.1 | 1.46 |
| 16 | $NiSO_4 \cdot 6H_2O$ | 0.101 | 48.2 | 37.3 | 85.5 | 1.29 |
| 17 | $ZnSO_4 \cdot 7H_2O$ | 0.101 | 48.9 | 32.2 | 81.1 | 1.52 |
| 18 | $AlK(SO_4)_2$ | 0.101 | 47.1 | 34.3 | 81.4 | 1.37 |
| 19 | $Ti_2(SO_4)_3$ | 0.101 | 48.7 | 34.1 | 82.8 | 1.43 |
| 20 | $Fe_2(SO_4)_3 \cdot 9H_2O$ | 0.101 | 48.0 | 30.2 | 78.2 | 1.59 |
| 21 | $In_2(SO_4)_3 \cdot 9H_2O$ | 0.101 | 53.5 | 36.4 | 89.9 | 1.47 |
| 22 | $Ce(SO_4)_2 \cdot 4H_2O$ | 0.101 | 51.1 | 39.6 | 90.7 | 1.29 |
| 23 | $(NH_2OH)_2H_2SO_4$ | 0.101 | 47.8 | 36.1 | 83.9 | 1.32 |
| 24 | benzenesulfonic acid | 0.101 | 53.8 | 31.2 | 85.0 | 1.72 |
| 25 | p-phenolsulfonic acid | 0.101 | 52.5 | 31.4 | 83.9 | 1.67 |
| 26 | p-aminosulfonic acid | 0.101 | 48.1 | 32.5 | 80.1 | 1.48 |
| 27 | strongly acidic type ion exchange resin Amberist 15 (available from Rohm & Haas Co.) | 0.101 | 51.1 | 37.1 | 88.2 | 1.38 |

EXAMPLES 28-30

With 10 g. (106 m. moles) of phenol were admixed the indicated ratios of 60 percent hydrogen peroxide and 4-methyl-2-pentanone in Table 5 and to the resulting mixture was added 0.070 g. of aluminum sulfate ($Al_2$-

($SO_4)_3.18H_2O$). The resulting mixture was reacted to 100° C. for 30 minutes in the same manner as in Example 1. Yields of catechol and hydroquinone are shown in Table 5.

Table 5

| Ex. | $H_2O_2$/phenol (molar ratio) | 4-methyl-2-pentanone/phenol (molar ratio) | CT yield (%) | HQ yield (%) | (CT+HQ) yield (%) | CT/HQ (molar ratio) |
|---|---|---|---|---|---|---|
| 28 | 0.190 | 0.290 | 42.6 | 29.6 | 72.2 | 1.44 |
| 29 | 0.065 | 0.110 | 48.6 | 37.1 | 85.7 | 1.31 |
| 30 | 0.037 | 0.056 | 52.9 | 42.3 | 95.2 | 1.25 |

EXAMPLES 31-33

10 g. (106 m. moles) of phenol, 0.222 g. (3.93 m. moles) of 60 percent hydrogen peroxide, 0.590 g. (5.90 m. moles) of 4-methyl-2-pentanone and 0.070 g. of aluminum sulfate ($Al_2(SO_4)_3.18H_2O$) were mixed together and the reacton was effected at the indicated temperature for the indicated period of time in Table 6. Yields of catechol and hydroquinone are shown in Table 6.

Table 6

| Ex. | Temperature (° C.) | Time (min.) | CT yield (%) | HQ yield (%) | (CT+HQ) yield (%) | CT/HQ (molar ratio) |
|---|---|---|---|---|---|---|
| 31 | 80 | 60 | 50.3 | 36.4 | 86.7 | 1.38 |
| 32 | 100 | 15 | 46.1 | 38.6 | 84.7 | 1.19 |
| 33 | 150 | 30 | 52.8 | 42.5 | 95.3 | 1.24. |

EXAMPLE 34

Into a 3l-volume flask equipped with a reflux condenser, a thermometer, a stirrer and an outlet for liquid were charged 2,000 g. (21.28 moles) of phenol, 117.0 g. (1.17 moles) of 4-methyl-2-pentanone and 60.1 g. (1.06 moles of a 60 percent hydrogen peroxide solution and the flask was maintained at 50° C. 25.8 g. of sodium bisulfate ($NaHSO_4.H_2O$) was added thereto and the flask was dipped in an oil bath at 110° C. so that the reaction could proceed. After 2 minutes and 1 hour from addition of the catalyst, 5 g. portions of the reaction mixture were withdrawn and analyzed by gas chromatography. After 10 hours, the whole reaction mixture was cooled to 50° C., the catalyst was removed by extraction with water and the residue was subjected to vacuum distillation to separate water, 4-methyl-2-pentanone, phenol, 61.6 g. (0.560 mole) of catechol and 41.7 g. (0.379 mole) of hydroquinone. Changes in yields of catechol and hydroquinone upon time lapse are summarized in Table 7.

Table 7

| Reaction period | CT yield (%) | HQ yield (%) | (CT+HQ) yield (%) | CT/HQ (molar ratio) |
|---|---|---|---|---|
| 2 min. | 53.4 | 36.1 | 89.5 | 1.48 |
| 1 hr. | 55.5 | 36.9 | 92.1 | 1.50 |
| 10 hrs. | 53.1 | 35.9 | 89.0 | 1.48. |

EXAMPLE 35

Into the same reaction vessel as in Example 34 were charged 1914 g. (20.36 moles) of phenol, 88.4 g. (0.884 mole) of 4-methyl-2-pentanone and 46.8 g. (0.827 mole) of a 60 percent hydrogen peroxide solution, and the flask was maintained at 90° C. To the resulting mixture was added 9.51 g. of aluminum sulfate ($Al_2(SO_4)_3.18H_2O$), and the flask was dipped in an oil bath at 115° C. for 30 minutes. Then, the reaction mixture was cooled to 50° C. and the catalyst suspending in the reaction mixture was removed by filtration. The filtrate was distilled in the same manner as in Example 34 to recover 45.6 g. (0.414 mole) of catechol and 36.5 g (0.332 mole) of hydroquinone. The total yield of catechol and hydroquinone was 90.2 percent.

EXAMPLE 36

50 g. of phenol (531 m. moles), 2.34 g. of 4-methyl-2-pentanone (23.4 m. moles), 1.31 g. (23.2 m. moles) of 60 percent hydrogen peroxide, and 0.4 mg. of sulfuric acid were mixed and the reaction was carried out at 50° C. for 15 minutes in the same way as in Example 1 and 1.23 g. of catechol and 0.93 g. of hydroquinone were obtained. The total yield of catechol and hydroquinone was 84.7 percent.

EXAMPLE 37

In the same reaction vessel as in Example 34, 1852 g. of phenol (19.68 ), 4.6 g. of 4-methyl-2-pentanone (0.046 ), 55.8 g. of 60 percent hydrogen peroxide (0.985 mole), and 0.10 g. of concentrated sulfuric acid were placed. The mixture was stirred at 50° C. in an oil bath for 10 minutes. After neutralization of sulfuric acid by adding 0.16 g. of 50 percent aqueous sodium hydroxide, the mixture was subjected to distillation under reduced perssure to fraction water, 3.7 g. of 4-methyl-2-pentanone, 1762 g. of phenol (18.72 moles), 56.8 g. of catechol (0.516 mole) and 38.5 g. of hydroquinone (0.350 mole). The total yield of the dihydric phenols based on hydrogen peroxide was 88.0 percent, and that based on phenol was 90.2 percent.

EXAMPLE 38

Into a 300 ml.-vlume four-necked flask, which was equipped with a reflux condenser, a thermometer, a stirrer and an outlet for liquid, were charged 150 g. (1390.0 m. moles) of m-cresol, 60.9 m. moles) of 4-methyl-3-pentanone and 2.56 g. (45.2 m. moles) of 60 percent hydrogen peroxide solution, and this flask was dipped in an oil bath at 120° C. The reaction mixture was reacted with stirring for 90 minutes. The reaction mixture was analyzed by gas chromatography to give 1.22 g. (9.8 m. moles) of 3-methylcatechol, 1.57 g. (12.7 m. moles) of 4-methylcatechol and 1.00 g. (8.1 m. moles) of 2-methylhydroquinone. The yeild of the dihydric alklphenols was 67.7 percent on hydrogen peroxide basis as defined below.

$$\text{Yield (\%) of the dihydric alkylphenols} = \frac{\text{millimole number of all dihydric alkylphenols produced}}{\text{millimole number of hydrogen peroxide charged}} \times 100.$$

EXAMPLE 39

The reacton was carried out in the same manner as in Example 38, except that 7.20 g. (60.0 m. moles) of methyl phenyl ketone was employed instead of the 4-methyl-2-pentanone. There were obtained 1.10 g. (8.9 m. moles) of 3-methylcatechol, 1.00 g. (8.1 m. moles) of 4-methylcatechol and 1.23 g. (9.9 m. moles) of 2-methylhydroquinone. The yield of dihydric alkyphenols (on hydrogen peroxide basis; the basis is frequently referred to hereinbelow) was 59.5 percent.

COMPARATIVE EXAMPLE 2

The reaction was carried out in the same manner as in Example 38, except that 4-methyl-2-pentanone was omitted. There were obtained 0.68 g. (5.5 m. moles) of 3-methycatechol, 0.80 g. (6.4 m. moles) of 4-methylcatechol and 0.94 g. (7.6 m. moles) of 2-methylhydroquinone. The yield of the dihydric alkyphenols was 43.1 percent.

EXAMPLE 40

Into the same reaction vessel as used in Example 38 were charged 150 g. (1390 m. moles) of o-cresol, 6.09 g. (60.9 m. moles) of 4-methyl-2-pentanone, 2.56 g. (45.2 m. moles) of 60 percent hydrogen peroxide solution and 0.40 g. of sulfuric acid and the reaction was carried out at 100° C. for 30 minutes in the same manner as in Example 38 to give 2.68 g. (21.5 m. moles) of 3-methylcatechol and 1.36 g. (10.9 m. moles) of 2-methylhydroquinone. The yield of the dihydric alkylphenols was 72.1 percent.

EXAMPLE 41

The reaction was carried out in the same manner as in Example 40, except that 150 g. (1390.0 m. moles) of m-cresol was used instead of o-cresol, to give 1.31 g. 10.5 m. moles) of 3-methycatechol, 2.29 g. (18.5 m. moles) of 4-methylcatechol and 1.74 g. (14.0 m. moles) of 2-methylhydroquinone. The yield of the dihydric alkylphenols was 95.4 percent.

EXAMPLES 42–47

Experiments were run in the same manner as in Example 40, except that p-cresol was employed instead of the o-cresol, and a reaction condition, a ketone and sort of catalyst were widely varied. The results are shown in Table 8.

COMPARATIVE EXAMPLE 2 (continued)

12.5 g. (125.0 m. moles) of 4-methyl-2-pentanone, 4.72 g. (83.3 m. moles) of 60 percent hydrogen peroxide solution, and 1.00 g. of sodium bisulfate (NaHSO$_4$.H$_2$O), and the reaction was carried out at 120° C. for 10 minutes to give 7.72 g. (46.5 m. moles) of 4-tert-butylcatechol. The yield of the dihydric alkylphenol was 55.8 percent.

EXAMPLE 50

150 g. (1000.0 m. moles) of p-tert-butylphenol, 5.00 g. (50.0 m. moles) of 4-methyl-2-pentanone, 1.89 g. (33.3 m. moles) of 60 percent hydrogen peroxide solution, and 0.40 g. of sulfuric acid were charged into a reaction vessel, and the reaction was carried out at 110° C. for 30 minutes in the same manner as in Example 40 to give 3.31 g. (20.0 m. moles) of 4-tert-butylcatechol. The yield of the didhyric alkylphenol was 60.0 percent.

EXAMPLE 51

Into a 3l-volume flask, which was equipped with a reflux condenser, a thermometer, a stirrer and an outlet for liquid, were charged 2160 g. (20.00 moles) of p-cresol, 90.0 g. (0.90 mole) of 4-methyl-2-pentanone, and 37.4 g. (0.66 mole) of 60 percent hydrogen peroxide solution, and the flask was maintained at 50° C. 1.5 g. of sulfuric acid were added thereto and the flask was dipped in an oil bath at 100° C. The reaction was carried out with stirring for 20 minutes. Thereafter, the sulfuric acid was extracted with water and the mixture was subjected to vacuum distillation to give 49.9 g. (0.403 mole) of 4-methylcatechol. The yield of dihydric alkylphenol was 61.0 percent.

EXAMPLE 52

In a reaction vessel equipped with a reflux condenser having a water-separating vessel, a thermometer, a stirrer, and an outlet for liquid were placed 100 g. (819 m.

Table 8

| Ex. No. | p-cresol (g) | 60% hydrogen peroxide solution (g) | H$_2$O$_2$/ p-cresol (molar) ratio | Ketone Sort | (g) | Ketone/ hydrogen peroxide (molar ratio) | Catalyst Sort | (g) | Reaction temp. (° C) | time (min.) | Product 4-methyl catechol yield (g) | (%) |
|---|---|---|---|---|---|---|---|---|---|---|---|---|
| 42 | 150 | 2.56 | 0.033 | 4-methyl-2-pentanone | 6.09 | 1.34 | H$_2$SO$_4$ | 0.40 | 100 | 5 | 3.54 | 63.2 |
| 43 | " | " | " | methyl phenyl ketone | 7.34 | " | " | " | " | 30 | 3.51 | 62.6 |
| 44 | " | 3.15 | 0.040 | cyclo-pentanone | 5.14 | 1.10 | " | " | " | " | 3.60 | 52.2 |
| 45 | " | 7.88 | 0.100 | 4-methyl-2-pentanone | 15.0 | 1.08 | In$_2$(SO$_4$)$_3$·9H$_2$O | 1.00 | 50 | 60 | 9.14 | 53.0 |
| 46 | " | 2.56 | 0.033 | 2,5-hexanedione | 6.97 | 1.34 | H$_2$SO$_4$ | 0.40 | 100 | 30 | 3.25 | 58.0 |
| 47 | " | " | " | 4-methyl-2-pentanone | 6.09 | " | strongly acidic ion exchange resin Amberist 15 | 1.00 | " | " | 3.28 | 58.6 |

EXAMPLE 48

The reaction was carried out in the same manner as in Example 40, except that 170 g. (1390.0 m. moles) of p-ethylphenol were employed instead of the o-cresol, thereby yielding 3.84 g. (27.8 m. moles) of 4-ethylcatechol. The yield of the dihydric alkylphenols was 61.6 percent.

EXAMPLE 49

Into the same reaction vessel as in Example 40 were charged 150 g. (1000.0 m. moles) of p-tert-butylphenol, moles) of 3,5-dimethylphenol, 4.1 g. (41 m. moles) of 4-methyl-2-pentanone, and 2.32 g. (41.0 m. moles) of 60 percent hydrogen peroxide. The vessel was immersed in an oil bath of 150° C. and stirred for 2 hours. During this time, water was continuously caught in the water-separating vessel. The reaction mixture was analyzed with gas chromatography. As products, 1.59 g. (11.5 m. moles) of 3,5-dimethylcatechol and 0.69 g. (5.0 m. moles) of 2,6-dimethylhydroquinone were obtained. The yield of the dihydric alkylphenols was 40.3 percent on hydrogen peroxide basis as defined in Example 38. The definition on the yields of dihydric alkylphenols is the same hereinbelow.

COMPARATIVE EXAMPLE 3

By following in the same manner as in Example 52, except that 4-methyl-2-pentanone was not added, the reaction was carried out and analyzed to give 1.02 g. (7.4 m. moles) of 3,5-dimethylcatechol and 0.55 g. (4.0 m. mole) of 2,6-dimethylhydroquinone. The yield of dihydric alkylphenols was 27.9 percent.

EXAMPLE 53

In a vessel used in Example 52 were placed 100 g. (819 m. moles) of 3,5-dimethylphenol, 3.61 g. (36.1 m. moles) of 4-methyl-2-pentanone, 2.88 g. (50.8 m. moles) of 60 percent hydrogen peroxide and 0.01 g. of sulfuric acid, and the mixture was reacted at 110° C. for 20 minutes in the same manner as in Example 52. The reaction mixture was analyzed with gas chromatography. As products, 3.19 g. (23.1 m. moles) of 3,5-dimethylcatechol and 2.24 g. (16.2 m. moles) of 2,6-dimethylhydroquinone were obtained. The yield of dihydric alkylphenols was 77.4 percent.

EXAMPLE 54

In a vessel used in Example 52 were placed 100 g. (819 m. moles) of 3,5-dimethylphenol, 2.97 g. (29.7 m. moles) of 4-methyl-2-pentanone, 2.52 g. (44.5 m. moles) of 60 percent hydrogen peroxide and 0.01 g. of sodium bisulfate ($NaHSO_4 \cdot H_2O$), and the mixture was treated at 110° C. for 20 minutes in the same manner as in Example 52. As products, 2.19 g. (15.9 m. moles) of 3,5-dimethylcatechol and 1.25 g. (9.08 m. moles) of 2,6-dimethylhydroquinone were obtained. The yield of dihydric alkylphenols was 56.1 percent.

EXAMPLE 55

By following in the same manner as in Example 53, except that 1.10 g. of strong acidic sulfonic type ion exchange resin Amberlist 15 (manufactured by Rohm & Haas Co.) was used instead of sulfuric acid, 2.88 g. (20.9 m. moles) of 3,5-dimethylcatechol and 1.74 g. (12.6 m. moles) of 2,6-dimethylhydroquinone were obtained. The yield of dihydric alkylphenols was 65.9 percent.

EXAMPLE 56

In a vessel used in Example 52 were placed 100 g. (819 m. moles) of 3,5-dimethylphenol, 2.64 g. (22.0 m. moles) of methylphenylketone, 1.81 g. (31.9 m. moles) of 60 percent hydrogen peroxide and 0.01 g. of sulfuric acid, and treated at 110° C. for 20 minutes in the same manner as in Example 52. 2.10 g. (15.2 m. moles) of 3,5-dimethylcatechol and 1.04 g. (7.5 m. moles) of 2,6-dimethylhydroquinone were obtained. The yield of the dihydric alkylphenols was 70.9 percent.

EXAMPLE 57

By following in the same manner as in Example 53, except that 0.25 g. (2.5 m. moles) of 4-methyl-2-pentanone was used instead of 3.61 g. (26.1 m. moles) of it, 3.09 g. (22.4 m. moles) of 3,5-dimethylcatechol and 2.07 g. (15 m. moles) of 2,6-dimethylhydroquinone were obtained. The yield of dihydric alkylphenols was 73.6 percent.

EXAMPLE 58

By following in the same manner as in Example 53, except that the amount of sulfuric acid was reduced from 0.01 g. to 0.001 g., and the reaction time was 30 minutes, 3.16 g, (22.9 m. moles) of 3,5-dimethylcatechol and 2.13 g. (15.4 m. moles) of 2,6-dimethylhydroquinone were obtained. The yield of dihydric alkylphenols was 75.4 percent.

EXAMPLE 59

By following in the same manner as in Example 53, except that 60 percent hydrogen peroxide was increased from 2.88 g. (50.8 m. moles) to 4.50 g. (79.4 m. moles), 4.69 g. (34.0 m. moles) of 3,5-dimethylcatechol and 2.75 g. (19.9 m. moles) of 2,6-dimethylhydroquinone were obtained. The yield of dihydric alkylphenols was 67.9 percent.

EXAMPLE 60

By following in the same manner as in Example 53, except that 100 g. (819 m. moles) of 2,4-dimethylphenol was used instead of 3,5-dimethylphenol, 2.50 g. (18.1 m. moles) of 3,5-dimethylcatechol were obtained. The yield of dihydric alkylphenol was 35.6 percent.

EXAMPLE 61

By following in the same manner as in Example 53, except that 100 g. (819 m. moles) of 2,5-dimethylphenol were used instead of 3,5-dimethylphenol, 1.45 g. (10.5 m. moles) of 3,6-dimethylcatechol and 1.85 g. (13.4 m. moles) of 2,5-dimethylhydroquinone were obtained. The yield of dihydric alkylphenols was 46.9 percent.

EXAMPLE 62

By following in the same manner as in Example 53, except that 100 g. (819 m. moles) of 2,6-dimethylphenol were used instead of 3,5-dimethylphenol, 1.04 g. (7.5 m. moles) of 2,6-dimethylhydroquinone were obtained. The yield of dihydric alkylphenol was 14.7 percent.

EXAMPLE 63

In a vessel used in Example 52 were placed 100 g. (735 m. moles) of 2,3,5-trimethylphenol, 2.31 g. (23.1 m. moles) of 4-methyl-2-pentanone, 2.61 g. (46.0 m. moles) of 60 percent hydrogen peroxide and 1.0 g. of indium sulphate ($In_2(SO_4)_3 \cdot 9H_2O$), and the mixture was treated at 100° C. for 60 minutes. 2.16 g. (14.2 m. moles) of 3,4,6-trimethylcatechol and 0.64 g. (4.2 m. moles) of 2,3,5-trimethylhydroquinone were obtained. The yield of dihydric alkylphenols was 40.0 percent.

EXAMPLE 64

By following in the same manner as in Example 63, except that 100 g. (735 m. moles) of 2,3,6-trimethylphenol were used instead of 2,3,5-trimethylphenol, 2.05 g. (13.5 m. moles) of 2,3,6-trimethylhydroquinone were obtained. The yield of dihydric alkylphenol was 29.4 percent.

EXAMPLE 65

In a 100 ml. flask equipped with a reflux condenser, a thermometer, stirrer and an outlet for liquid were charged 50 g. (530 m. moles) of phenol, 5 g. (5.7 m. moles) of 1,1,1,3,3,3-hexachloro-2-propanone, 1.48 g. (26.1 m. moles) of 60 percent hydrogen peroxide and 0.02 g. of 98 percent sulfuric acid. The mixture which was formed was reacted for 30 minutes by dipping the flask into an oil bath at 100° C. The resulting reaction mixture was analyzed by gas chromatography, thus obtaining 1.46 g. (13.3 m. moles) of catechol and 0.60 (5.5 m. moles) of hydroquinone. The total yield of these dihydric phenols was 72 percent based on the hydrogen peroxide used.

EXAMPLE 66

The experiment was carried out in the same manner as in Example 65, except that 0.50 g. (5.43 m. moles) of 1-chloro-2-propanone was added instead of 1,1,1,3,3,3-hexachloro-2-propanone. Analysis showed that 1.38 g. (12.6 m. moles) of catechol and 0.58 g. (5.3 m. moles) of hydroquinone were obtained. The yield of these dihydric phenols was 68.4 percent based on the hydrogen peroxide used.

EXAMPLE 67

The experiment was carried out in the same manner as in Example 65, except that 1.12 g. (5.09 m. moles) of 1,1,1,3,3,3-hexafluoro-2-propanone trihydrate were added instead of 1,1,1,3,3,3-hexachloro-2-propanone. Analysis showed that 1.46 g. (13.3 m. moles) of catechol and 0.81 g. (7.4 m. moles) of hydroquinone were obtained. The yield of these dihydric phenols was 79.3 percent.

As described and illustrated above, the specified dihydric phenols can be formed by oxidizing the indicated monohydric phenols with hydrogen peroxide in a reaction charge consisting essentially of a monohydric phenol, hydrogen peroxide and a specified ketone.

We claim:
1. A process preparing a dihydric phenol having the formula:

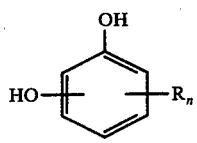

wherein R represents a lower alkyl radical having 1–6 carbon atoms and each R may be the same or different, and $n$ represents zero or an integer of from 1 to 4 and when $n$ is 3 or 4 not all of the 2-, 4- and 6-positions are occupied with the said alkyl radicals,
which comprises oxidizing, at a temperature of from 45° C. to 200° C. in the absence of a catalyst, a monohydric phenol having the formula

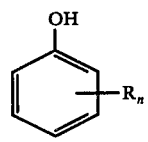

wherein R and $n$ have the same meanings as above, with hydrogen peroxide in the presence of a ketone selected from the group consisting of:
i. a ketone having 3–20 carbon atoms represented by the following formula:

wherein $R_1$ and $R_2$, which may be the same or different, each represents straight or branched alkyl groups of 1–18 carbon atoms or a phenyl group, the alkyl groups being unsubstituted or substituted with a halogen atom, and at least one of $R_1$ and $R_2$ may be an aliphatic group having an unsaturated bond;

ii. a diketone having 3–20 carbon atoms represented by the following formula:

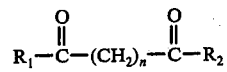

wherein $n$ is zero or an integer of 1–16, inclusive, and $R_1$ and $R_2$ have the same meanings as above; and iii. a cycloketone having the following formula:

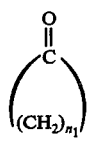

wherein $n_1$ represents an integer of 4–11, inclusive, 2-ethyl-1-cyclopentanone or 2-methyl-1-cyclohexanone; the molar ratio of hydrogen peroxide to said monohydric phenol being from 0.01 to 0.50.

2. The process of claim 1, wherein the monohydric phenol is phenol.

3. The process of claim 1, wherein $n$ is 1 in the monohydric phenol.

4. The process of claim 1, wherein $n$ is from 2 to 4 in the monhydric phenol.

5. The process of claim 1, wherein the reaction is carried out at a temperature of from 0° to 250° C.

6. The process of claim 5, wherein the reaction is carried out at a temperature of 45° to 200° C.

7. The process of claim 1, wherein the concentration of hydrogen peroxide used is at least from 30 to 60 percent.

8. The process of claim 1, wherein the molar ratio of ketone to hydrogen peroxide is from 0.005 to 20.

9. The process of claim 1, wherein the ketone is 4-methyl-2-pentanone.

10. The process of claim 1, wherein the ketone is methyl phenyl ketone.

11. A process for preparing a dihydric phenol having the formula:

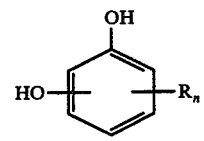

wherein R represents a lower alkyl radical having 1–6 carbon atoms and each R may be the same or different, and $n$ represents zero or an integer of from 1 to 4 and when $n$ is 3 or 4 not all of the 2-, 4- and 6-positions are occupied with the said alkyl radicals,
which comprises oxidizing, at a temperature of from 45° C. to 200° C., a monohydric phenol having the formula

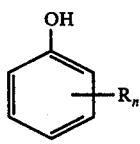

wherein R and n have the same meanings as above, with hydrogen peroxide in the presence of a ketone selected from the group consisting of:

i. a ketone having 3-20 carbon atoms represented by the following formula:

$$R_1-CO-R_2$$

wherein $R_1$ and $R_2$, which may be the same or different, each represents straight or branched alkyl groups of 1-18 carbon atoms or a phenyl group, the alkyl groups being unsubstituted or substituted with a halogen atom, and at least one of $R_1$ and $R_2$ may be an aliphatic group having an unsaturated bond;

ii. a diketone having 3-20 carbon atoms represented by the following formula:

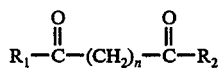

wherein $n$ is zero or an integer of 1-16, inclusive, and $R_1$ and $R_2$ have the same meanings as above; and

wherein $n_1$ represents an integer of 4-11, inclusive, 2-ethyl-1-cyclopentanone or 2-methyl-1-cyclohexanone;

and a catalytic amount of a catalyst selected from the group consisting of sulfuric acid, a salt thereof, a sulfonic acid and a salt thereof; the molar ratio of hydrogen peroxide to said monohydric phenol being from 0.01 to 0.50.

12. The process of claim 11, wherein the amount of catalyst is not less than 0.0001 percent by weight with respect to the weight of the monohydric phenol.

13. The process of claim 11, wherein the catalyst is sulfuric acid.

14. The process of claim 11, wherein the catalyst is sodium bisulfate.

15. The process of claim 11, wherein the catalyst is indium sulfate.

16. The process of claim 11, wherein the catalyst is aluminum sulfate.

17. The process of claim 11, wherein the catalyst is potassium acid sulfate.

* * * * *

UNITED STATES PATENT AND TRADEMARK OFFICE
CERTIFICATE OF CORRECTION

PATENT NO. : 4,078,006
DATED : March 7, 1978
INVENTOR(S) : SUMIO UMEMURA et al

It is certified that error appears in the above-identified patent and that said Letters Patent are hereby corrected as shown below:

Column 1, line 40: rewrite "fur" as ---für---.

Column 1, line 52: before "acid", "and" should be ---an---.

Column 7, Table 2, Example 5: below "5", delete "dione" and re-insert it in the next column below "2,5-hexane-".

Column 9, line 1: replace "to" with ---at---.

Column 10, line 21: after "0.046", insert ---mole)---.

Column 10, line 22: delete ")".

Column 10, line 28: rewrite "perssure" as ---pressure---.

Column 10, line 37: replace "vlume" with ---volume---.

Column 10, line 40: "60.9 m. moles)" should be rewritten as ---6.09 g. (60.9 m. moles)---.

Column 10, line 48: rewrite "yeild" as ---yield---, and "alklphenols" as ---alkylphenols---.

Column 10, line 66 and Column 11, line 8: rewrite "alkyphenols" as ---alkylphenols---.

Column 11, line 27: rewrite "methycatechol" as ---methylcatechol---.

UNITED STATES PATENT AND TRADEMARK OFFICE
CERTIFICATE OF CORRECTION

PATENT NO. : 4,078,006  Page 2 of 2
DATED : March 7, 1978
INVENTOR(S) : SUMIO UMEMURA et al It is certified that error appears in the above-identified patent and that said Letters Patent are hereby corrected as shown below:

Column 12, lines 5-6: rewrite "butylcathechol" as
---butylcatechol---.

Column 12, line 17: rewrite "didhydric" as ---dihydric---.

Column 16, line 34: rewrite "monhydric" as ---monohydric---.

Column 18, lines 5-9 (Claim 11):

replace "
$$\begin{array}{c} O \\ \parallel \\ C \\ | \\ (CH_2)_{n_1} \end{array}$$
" with ---
$$\begin{array}{c} O \\ \parallel \\ C \\ / \quad \backslash \\ (CH_2)_{n_1} \end{array}$$
---.

Signed and Sealed this

Eighteenth Day of September 1979

[SEAL]

Attest:

LUTRELLE F. PARKER
Attesting Officer    Acting Commissioner of Patents and Trademarks